United States Patent [19]

Fernandez-Aceytuno

[11] Patent Number: 5,735,869
[45] Date of Patent: Apr. 7, 1998

[54] BALLOON CATHETER AND STENT DELIVERY DEVICE

[75] Inventor: Alfonso Medina Fernandez-Aceytuno, E-Las Palmas de Gran Canaria, Spain

[73] Assignee: Schneider (Europe) A.G., Bulach, Switzerland

[21] Appl. No.: 548,786

[22] Filed: Oct. 26, 1995

Related U.S. Application Data

[63] Continuation-in-part of Ser. No. 547,186, Oct. 24, 1995, Pat. No. 5,628,755.

[30] Foreign Application Priority Data

Nov. 30, 1994 [EP] European Pat. Off. ............ 94118900

[51] Int. Cl.⁶ ............................................. A61M 29/00
[52] U.S. Cl. ...................... 606/194; 606/198; 604/96; 604/103
[58] Field of Search ................... 604/96–104; 606/1, 606/108, 191–200; 600/201, 204, 207

[56] References Cited

U.S. PATENT DOCUMENTS

| | | | |
|---|---|---|---|
| 4,824,435 | 4/1989 | Giesy et al. | 604/49 |
| 5,171,305 | 12/1992 | Schickling et al. | 604/271 |
| 5,201,757 | 4/1993 | Heyn et al. | 606/198 |
| 5,242,399 | 9/1993 | Lau et al. | 604/104 |
| 5,246,421 | 9/1993 | Saab | 604/96 |
| 5,312,356 | 5/1994 | Engelson et al. | 604/164 |
| 5,391,172 | 2/1995 | Williams et al. | 606/108 |
| 5,545,209 | 8/1996 | Roberts et al. | 606/108 |

FOREIGN PATENT DOCUMENTS

| | | |
|---|---|---|
| 0335341 | 10/1989 | European Pat. Off. . |
| 0335341 B1 | 10/1989 | European Pat. Off. . |
| 0408245 | 1/1991 | European Pat. Off. . |
| 0408245A1 | 1/1991 | European Pat. Off. . |
| 0466518A2 | 1/1992 | European Pat. Off. . |
| 0678307 A2 | 10/1995 | European Pat. Off. . |
| 9401050 | 4/1994 | Spain . |
| 9500456 | 2/1995 | Spain . |
| 9508965 | 4/1995 | WIPO . |
| 9619256 | 6/1996 | WIPO . |
| 9640349 | 12/1996 | WIPO . |

OTHER PUBLICATIONS

United States Patent application Ser. No. 08/547,186, filed Oct. 24, 1995, which is commonly owned by the assignee of this application.

*Primary Examiner*—Glenn K. Dawson
*Attorney, Agent, or Firm*—Peter C. Richardson; Lawrence C. Akers; Philip C. Strassburger

[57] ABSTRACT

A stent delivery system for a balloon expandable stent includes a balloon catheter with a tubular shaft and an elongated dilatation balloon. The tubular shaft has a guidewire lumen with an entry for the guidewire distal of the balloon and an exit for the guidewire proximal of the balloon. A sleeve for preventing expansion of balloon segments is mounted on the tubular shaft with a distal end surrounding a portion of the proximal end of the balloon and a proximal end removably attached to a portion of the tubular shaft.

12 Claims, 4 Drawing Sheets

BALLOON CATHETER AND STENT DELIVERY DEVICE

This is a continuation-in-part of application Ser. No. 08/547,186, filed on Oct. 24, 1995, now U.S. Pat. No. 5,628,755.

BACKGROUND OF THE INVENTION

This invention relates to a balloon catheter comprising a tubular shaft having a proximal end and a distal end, an elongated dilatation balloon mounted on said tubular shaft in the vicinity of the distal end thereof, and means secured on the tubular shaft for preventing expansion of balloon segments.

The invention also relates to a stent delivery system for a balloon expandable stent, comprising a balloon catheter with a tubular shaft having a proximal end and a distal end, and an elongated dilatation balloon mounted on said tubular shaft in the vicinity of the distal end thereof.

Balloon catheter technology makes use of balloons of fixed lengths, whereby the great number of medical procedures requiring balloon catheter technology makes it necessary to rely on several catheters of different balloon length. Where a procedure requires, for exemply, two differently sized balloons, it is necessary to change balloon catheters or to act sequentially with the one length balloon available. Changing balloon catheter is costly while sequential action with the available balloon length may be a time-consuming and potentially risky procedure which may lead to injury of the patient or insufficient dilatations.

The balloon catheter is also an instrument of common use as a mechanism for transporting and applying a balloon expandable prosthesis, called a stent, for maintaining the patency of a vessel. The length of the balloon must be chosen as a function of the length of the stent, to avoid inappropriate expansion of the stent or damage to the vessel. This may also lead to the costly need of a plurality of balloon catheters to correctly and safely apply the stents.

U.S. Pat. No. 5,246,421 refers to a method of treating obstructed regions of bodily passages which provides for use of balloon catheters with adjustable length balloons. Accordingly, this document teaches the use of a balloon catheter in which an adjustable sheath is externally manipulated to partially surround and contain the dilatation balloon segment of the catheter in situ during a treatment procedure. By external manipulations sliding the sheath forwardly and backwardly to expose a predetermined length of the balloon segment prior to inflating the balloon, various balloon lengths can be obtained. The catheter body can comprise an elongated tube and a balloon attached by both its neck portions to two axially spaced locations on the elongated tube; the catheter can also have a catheter body defining a lumen with a balloon terminating such a body as an integral one piece assembly having a closed end. The document outlines that the described technology can be modified or tuned to be compatible with virtually any catheter constructions, including over the wire catheters constructions, including over the wire catheters and fixed wire catheters. In order to avoid creep of the sheath during or after inflation of the balloon tending to uncover more balloon than originally selected, the position of the sheath may be firmly fixed, for example by a clamping device, prior to inflation of the balloon. The mere fact that the sheath is externally manipulated creates a substantial complication in the catheter construction, and the risk of having the sheath clogged up. In addition, the system is relatively cumbersome and rigid due to the multiplicity of elements resulting from the externally manipulated sheath over the catheter shaft, which may cause some difficulties for the treatment of tortuous or narrow vessels. And there may also be a friction problem between the sheath and catheter shaft which may add difficulties to the external manipulation of the sheath. There is no suggestion in this document that the moving sheath and resulting variable length balloon catheter could be envisaged as a system for matching the balloon length requirements for stent delivery.

It is an object of this invention to overcome the drawbacks and limitations of the prior art equipment by proposing a balloon catheter which is highly versatile, simple to manufacture and easy to use. A further object of the invention is to propose a stent delivery system which is also highly versatile, simple to manufacture, and easy to use.

SUMMARY OF THE INVENTION

In sum, the present invention relates to a balloon catheter having a tubular shaft with a proximal end and a distal end and an elongated dilatation balloon with proximal and distal ends. The balloon is mounted on the tubular shaft in the vicinity of the distal end thereof, with means secured on the tubular shaft for preventing expansion of balloon segments. The tubular shaft has a guidewire lumen with an entry for the guidewire distal of the balloon and an exit for the guidewire distal of the proximal end of the tubular shaft and means for preventing expansion of balloon segments attached to the tubular shaft either distal of the exit for the guidewire if said exit is proximal of the balloon or proximal of the exit for the guidewire if said exit is distal of the balloon. The means for preventing expansion of balloon segments may be removably or permanently attached to the tubular shaft. The means for preventing expansion of balloon segments may be a sleeve having proximal and distal ends one of which is surrounding a portion of the tubular shaft in the vicinity of the balloon and the other of which is surrounding a portion of the balloon. The balloon catheter may further have latch means cooperating with catch means for attaching one end of the sleeve to the portion of the tubular shaft surrounded by that end of the sleeve. The balloon catheter may further have elastic balloon jacket means for enclosing a portion of the balloon, the jacket means having a proximal end and a distal end, and wherein one of the ends is adapted to the tubular shaft and the other of the ends is adapted to the means for preventing expansion of balloon segments.

The present invention also relates to a stent delivery system for a balloon expandable stent, having a balloon catheter with a tubular shaft with a proximal end and a distal end, and an elongated dilatation balloon with proximal and distal ends. The balloon is mounted on the tubular shaft in the vicinity of the distal end thereof. The tubular shaft has a guidewire lumen with an entry for the guidewire distal of the balloon and an exit for the guidewire distal of the proximal end of the tubular shaft, and means for preventing expansion of balloon segments attached to the tubular shaft either distal of the exit for the guidewire if said exit is proximal of the balloon or proximal of the exit for the guidewire if said exit is distal of the balloon. The means for preventing expansion of balloon segments may be removably or permanently attached to the tubular shaft. The means for preventing expansion of balloon segments may comprise a sleeve having proximal and distal ends one of which is surrounding a portion of the tubular shaft in the vicinity of the balloon and the other of which is surrounding a portion of the balloon. The stent delivery system may further have latch means cooperating with catch means for attaching one end of the sleeve to the portion of the tubular shaft surrounded by that end of the sleeve. The stent delivery system may further have elastic balloon jacket means for enclosing a portion of the balloon, the jacket means having a proximal end and a distal end, and wherein one of the ends is adapted to the tubular shaft and the other of the ends is adapted to the means for preventing expansion of balloon segments.

Accordingly, either for primary usage of the balloon catheter, i.e. for dilatation of stenoses, or for stent delivery of a balloon expandable stent, it is very simple and easy to modify the length of the balloon while taking full advantage of the fast, efficient and widely practised technology known under the name MONORAIL®. There is no external manipulation of the means for preventing expansion of balloon segments during introduction, withdrawal or use of the balloon catheter, either for stenosis dilatation or for stent delivery within the patient's vessel. The construction of the balloon catheter remains simple, without unwanted diameter consuming multiplicity of superposed elements all along the tubular shaft. And there is no friction generating motion of elements.

In practice, for stenosis dilatation purposes, the doctor may simply modify a standard balloon catheter before dilatation of a stenosis, or he may proceed to a first dilatation with the original length of the balloon, and then withdraw the balloon catheter as usual along the guidewire, modify the operational length of the balloon by attaching the means for preventing expansion of balloon segments to the tubular shaft, and then insert as usual the balloon catheter over the guidewire to rapidly reach the stenosis which has to be treated with a reduced balloon length. For stent delivery purposes, he may modify a standard balloon catheter for delivering a stent in a dilated stenosis, or he may as well effect the stenosis dilatation with the available dilatation balloon and then withdraw the balloon catheter along the guidewire, attach the means for preventing expansion of balloon segments to the catheter shaft, install the stent in collapsed condition on the appropriate balloon segment, and then reinsert as usual the stent equipped balloon catheter over the guidewire to reach the required location in the patient's vessel and expand the stent via balloon inflation.

The means for preventing expansion of balloon segments may be removably or permanently attached to the tubular shaft. Removable means allow selection of balloon length by the doctor and replacement of the expansion preventing means to meet his requirements on the basis of standard balloon length. Permanently attached means permit reducing the number of balloon sizes by equipment of a series of balloon catheters having standard size balloons with different expansion preventing means.

Where the expansion preventing means comprise a sleeve having proximal and distal ends one of which is surrounding a portion of the tubular shaft in the vicinity of the balloon and the other of which is surrounding a portion of the balloon, the expansion preventing means can be realized very economically and the sleeve may be permanently attached to the tubular body for series of balloon catheters with standard sizes balloons or removably attached thereto, for example for the supply of a set of sleeves of different lengths to manage expansion prevention of balloon segments of different lengths.

A simple, efficient and inexpensive attachment of the sleeve may be achieved by latch means cooperating with catch means for attaching one end of the sleeve to the portion of the tubular shaft surrounded by that end of the sleeve.

In order to protect the vessel wall against fluid jets which may be caused by balloon ruptures due to the very high pressures which are required in particular for stent expansion, there is provided for elastic balloon jacket means for enclosing a portion of the balloon, said jacket means having a proximal end and a distal end, and one of said ends being affixed to the tubular shaft and the other of said ends being affixed to the means for preventing expansion of balloon segments. In that way, the elastic jacket means dampen any jets which may arise from balloon rupture and they protect the vessel wall. These jacket means also protect the balloon skin from rupture which may be caused by a sharp-edged stent. Upon deflation of the balloon, the jacket means help folding back of the balloon.

These and other objects will become readily apparent from the following detailed description with reference to the accompanying drawings which show, diagrammatically and by way of example only various embodiments of the invention.

DETAILED DESCRIPTION OF THE INVENTION

Figure 1:
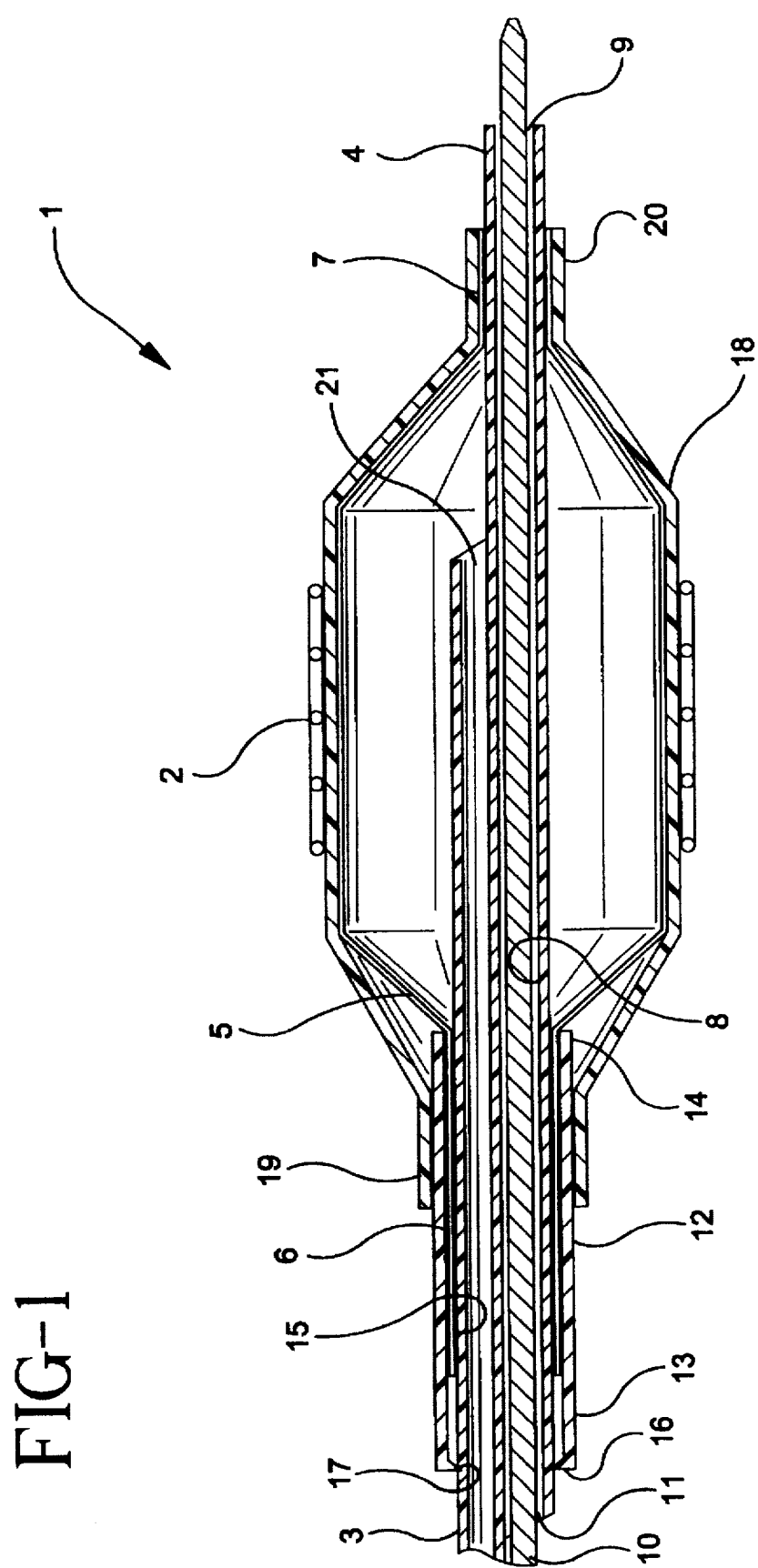
FIG. 1 is a cross-sectional view of a stent delivery system embodying the invention.

The stent delivery system shown in FIG. 1 comprises a balloon catheter 1 intended for handling a balloon expandable stent 2 in a body vessel such as, for instance, a coronary. This balloon catheter comprises a tubular shaft 3 having a proximal end (not shown) and a distal end 4. An elongated dilatation balloon 5 (shown in inflated condition) with proximal and distal ends 6 and 7 is mounted on the tubular shaft 3 in the vicinity of its distal end 4. The balloon 5 is affixed to the tubular shaft as commonly in the art.

The tubular shaft 3 comprises a fluid supply lumen 21 for balloon inflation and a guidewire lumen 8 with an entry 9 for the guidewire 10 distal of the balloon 5 and an exit 11 for the guidewire 10 distal of the proximal end (not shown) of the tubular shaft 3.

Figure 3:
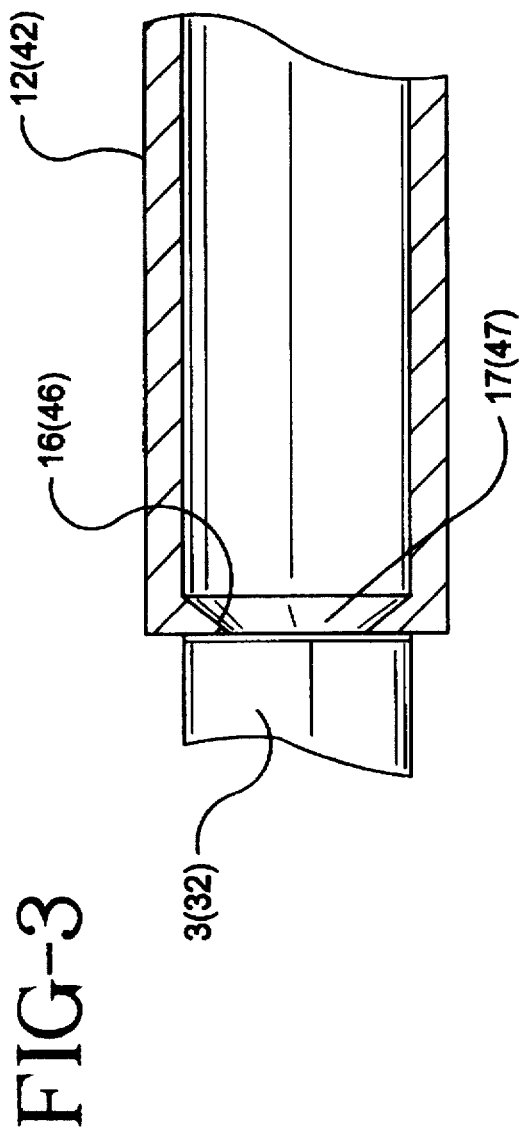
FIG. 3 is a cross-sectional view of a detail of either the stent delivery system of FIG. 1 or the balloon catheter of FIG. 2.

Means for preventing expansion of balloon segment are attached to the tubular shaft 3 distal of the exit 11 for the guidewire 10 which is proximal of the balloon 5. These means for preventing expansion of balloon segments comprise a not distensible sleeve 12 mounted on tubular shaft 3 and having proximal and distal ends 13 and 14. the distal end 14 of sleeve 12 is surrounding a portion 15 of the proximal end 6 of balloon 5 thereby preventing its expansion. The proximal end 13 of sleeve 12 is surrounding a portion of the tubular shaft 3 and comprises a circular constriction 16 (FIG. 3) engaged into a corresponding circular groove 17 of tubular shaft 3 to firmly but removably attach the proximal end of sleeve 12 to the tubular shaft 3, thereby preventing its displacement during inflation of the balloon as well as during insertion and withdrawal of the catheter 1 into and from the body vessel.

An elastic balloon jacket 18 encloses a portion of balloon 5, having its proximal end 19 affixed, for instance adhered, to the distal end 14 of sleeve 12, and its distal end 20 elastically squeezing the distal end of tubular shaft 3, at the location of the distal end 7 of balloon 5.

The balloon expandable stent 2 is mounted on the balloon jacket 18, as commonly in the art for balloon delivery of balloon expandable stents.

To install the sleeve 12 on the balloon catheter 1 it suffices to engage the sleeve over the distal end of the balloon catheter and to slide it along the catheter and balloon up to clicking the constriction 16 into groove 17. The removal of the sleeve is achieved by the opposite operation.

Figure 2:
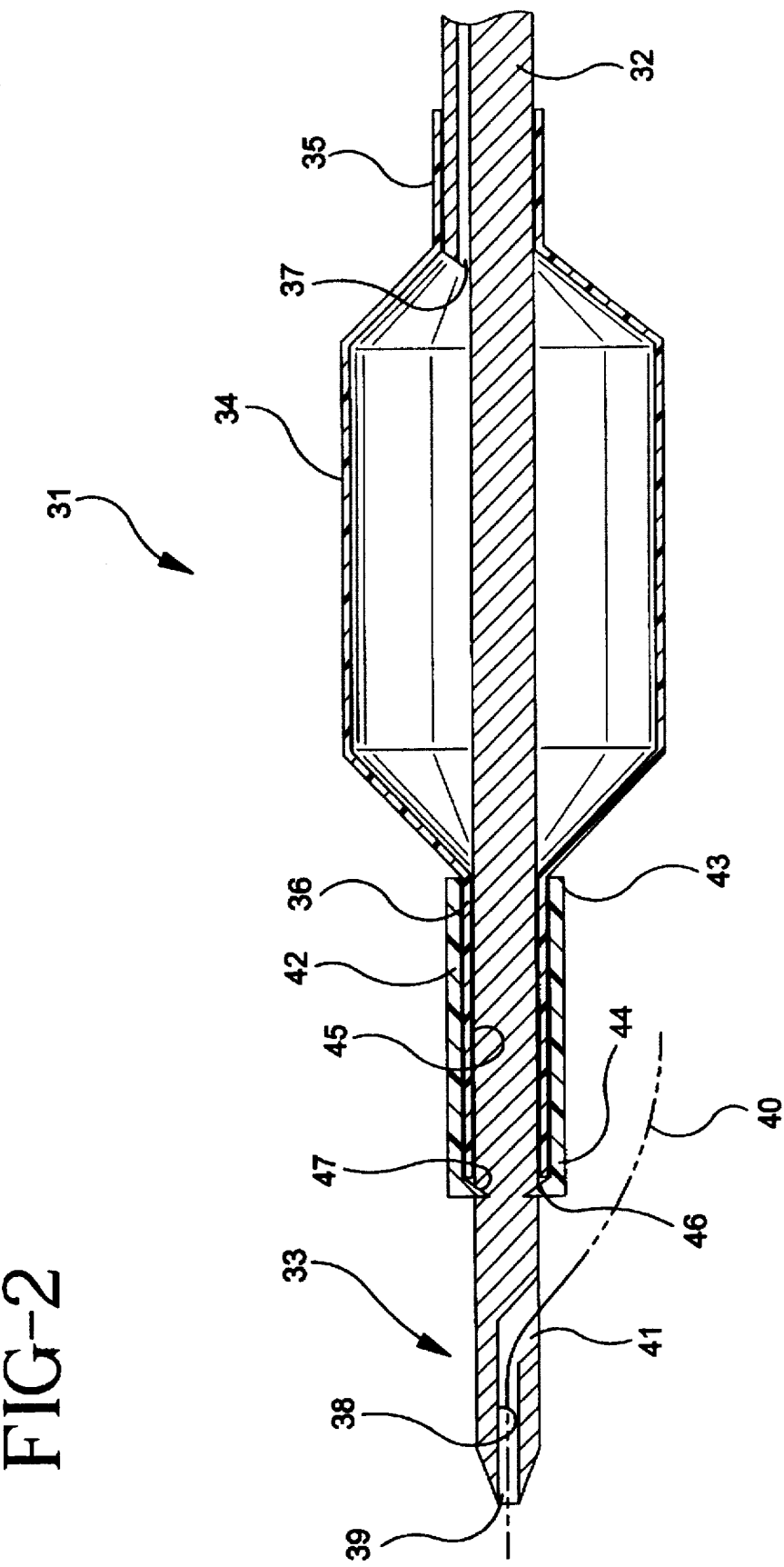
FIG. 2 is a cross-sectional view of a balloon catheter embodying the invention.

The balloon catheter 31 shown in FIG. 2 comprises a tubular shaft 32 having a proximal end (not shown) and a distal end 33. An elongated dilatation balloon 34 (shown in inflated condition) having a proximal end 35 and a distal end 36 is mounted and affixed, in conventional manner, on the tubular shaft 32 in the vicinity of its distal end 33.

The tubular shaft 32 comprises an inflation lumen 37 for the balloon 34 and a guidewire lumen 38 having an entry 39 for the guidewire 40 distal of the balloon 34 and an exit for the guidewire 40 distal of the proximal end (not shown) of the tubular shaft 32.

Means for preventing expansion of balloon segments are attached to the tubular shaft 32 proximal of the exit 41 for the guidewire 40 which is distal of the balloon 34. These means for preventing expansion of balloon segments comprise a not distensible sleeve 42 mounted on tubular shaft 32 and having proximal and distal ends 43 and 44. The proximal end 43 of sleeve 42 is surrounding a portion 45 of the distal end 36 of balloon 34 for preventing its expansion. The distal end 44 of sleeve 42 is surrounding a portion of tubular shaft 32 and comprises a circular constriction 46 (see also FIG. 3) engaged into a corresponding circular groove 47 of tubular shaft 32 to firmly and removably attach the distal end of sleeve 42 to the tubular shaft 32 to prevent any displacement thereof during inflation of the balloon as well as during insertion and withdrawal of the balloon catheter 31 into and from a body vessel.

As for the stent delivery system of FIG. 1, installation of sleeve 42 on the balloon catheter 31 is achieved by merely engaging the sleeve 42 over the distal end of tubular shaft 32 and to slide it along the tubular shaft and distal end 36 of balloon 34 until constriction 46 clicks into circular groove 47. Removal of the sleeve is effected by the opposite motion.

Variants may be envisaged without departing from the scope of the invention.

For instance, the stent delivery system according to FIG. 1 could be used as a balloon catheter for dilatation of stenoses, with or without the balloon jacket. Similarly, the balloon catheter of FIG. 2 may be used as a stent delivery system, with or without the addition of the balloon jacket.

The balloon jacket 18 shown in FIG. 1 may be attached differently to the tubular shaft 2, for instance with its distal end 20 adhered at the location of the distal end 7 of balloon 5 and with the proximal end 19 elastically squeezing the distal end of tubular shaft 2 at the location of the proximal end 6 of balloon 5.

Figure 4:
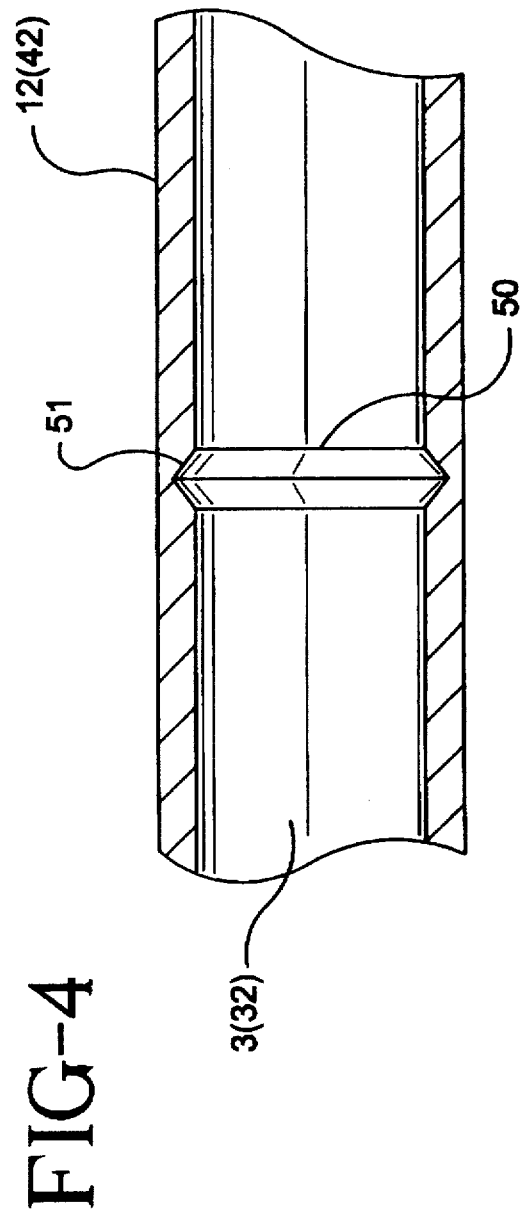
FIGS. 4, 5 and 6 are cross-sectional views showing variants of the detail of FIG. 3.
Figure 5:
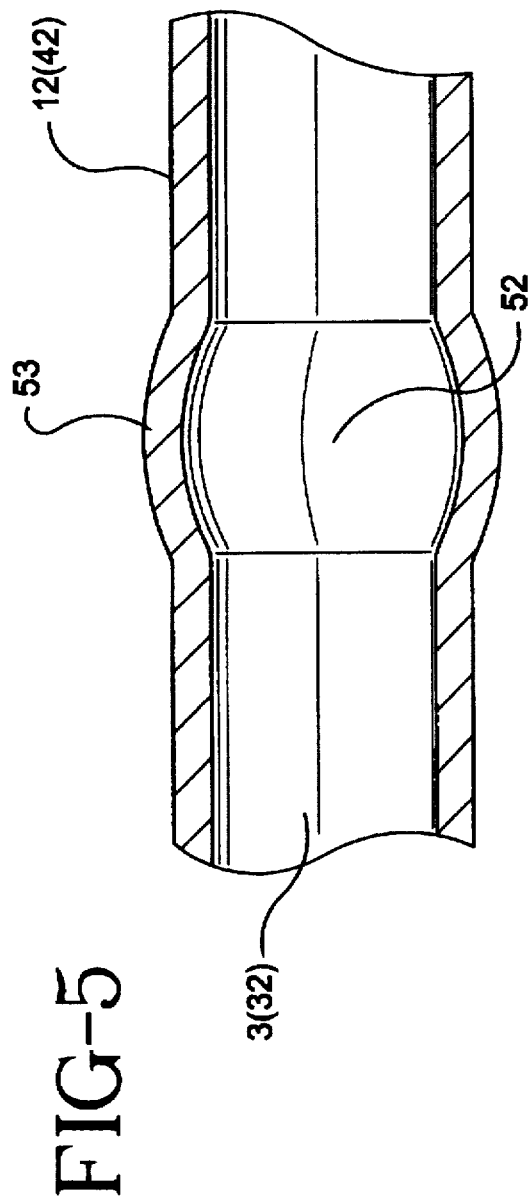
Figure 6:
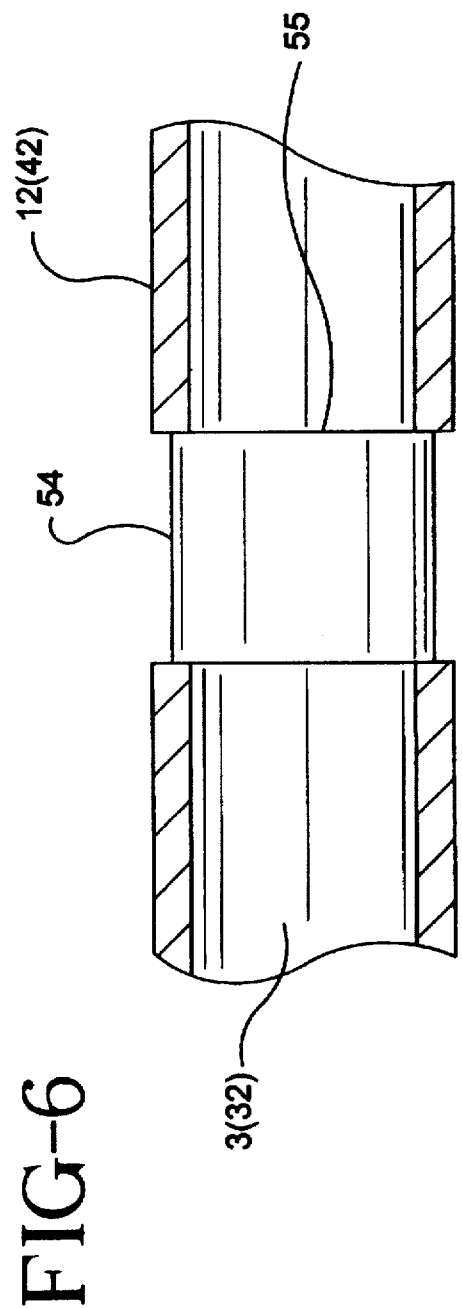

Another combination of catch means could be used to replace the constriction 16 (46) and groove 17 (47) shown in FIGS. 1 and 2 to attach one end to sleeve 12 (42) to the tubular shaft 3 (32). For example, as shown in FIG. 4, a circular rib 50 arranged on the tubular shaft 3 (32) for cooperating with a circular groove 51 in the sleeve 12 (42). Or, as shown in FIG. 5, rounded circular rib 52 on the tubular shaft 3 (32) cooperating with a correspondingly shaped embossing 53 in the sleeve 12 (42). It is also possible to have two or more grooves for cooperation with one rib in order to obtain various selectable positions for the sleeve. A further possibility would be to have matching threads on the tubular shaft and in the corresponding end of the sleeve. A further possibility is the use of a belt 54 (FIG. 6) squeezing sleeve 12 (42) to cause its deformation into a corresponding groove 55 of the tubular shaft 3 (32).

When permanent attachment of the sleeve to the tubular shaft is required, this may be achieved by adhesion or welding of the corresponding portion of the sleeve. This means for preventing expansion of balloon segments my be other than a sleeve, for example, a clamp attached to the tubular shaft either distal of the exit for the guidewire if said exit is proximal of the balloon or proximal of the exit for the guidewire if said exit is distal of the balloon.

I claim:

1. A balloon catheter comprising: a tubular shaft having a proximal end and a distal end, an elongated dilatation balloon with proximal and distal ends, said balloon being mounted on said tubular shaft in the vicinity of the distal end thereof, a first means secured on the tubular shaft for preventing expansion of balloon segments and a second means on the first means cooperating with a third means on the tubular shaft for adjustably fixing the first means on the tubular shaft at different longitudinal positions wherein the tubular shaft comprises a guidewire lumen with an entry for the guidewire distal of the balloon and an exit for the guidewire distal of the proximal end of the tubular shaft and wherein the first means for preventing expansion of balloon segments is either distal of the exit for the guidewire if said exit is proximal of the balloon or proximal of the exit for the guidewire if said exit is distal of the balloon.

2. A balloon catheter according to claim 1, wherein the first means for preventing expansion of balloon segments is removably attached to the tubular shaft.

3. A balloon catheter according to claim 1, wherein the first means for preventing expansion of balloon segments is slidably attached to the tubular shaft.

4. A balloon catheter according to claim 1, wherein the first means for preventing expansion of balloon segments comprise a sleeve having proximal and distal ends one of which is surrounding a portion of the tubular shaft in the vicinity of the balloon and the other of which is surrounding a portion of the balloon.

5. A stent delivery system for a balloon expandable stent comprising: a balloon catheter with a tubular shaft having a proximal end and a distal end, and an elongated dilatation balloon with proximal and distal ends, said balloon being mounted on said tubular shaft in the vicinity of the distal end thereof, a first means secured on the tubular shaft for preventing expansion of balloon segments and a second means on the first means cooperating with a third means on the tubular shaft for adjustably fixing the first means on the tubular shaft at different longitudinal positions wherein the tubular shaft comprises a guidewire lumen with an entry for the guidewire distal of the balloon and an exit for the guidewire distal of the proximal end of the tubular shaft, and wherein the first means for preventing expansion of balloon segments is either distal of the exit for the guidewire if said exit is proximal of the balloon or proximal of the exit for the guidewire if said exit is distal of the balloon.

6. A stent delivery system according to claim 5, wherein the first means for preventing expansion of balloon segments is removably attached to the tubular shaft.

7. A stent delivery system according to claim 5, wherein the first means for preventing expansion of balloon segments is slidably attached to the tubular shaft.

8. A stent delivery system according to claim 5, wherein the means for preventing expansion of balloon segments comprise a sleeve having proximal and distal ends one of which is surrounding a portion of the tubular shaft in the vicinity of the balloon and the other of which is surrounding a portion of the balloon.

9. A balloon catheter comprising:

a tubular shaft having a proximal end and a distal end, an elongated dilatation balloon with proximal and distal ends, said balloon being mounted on said tubular shaft in the vicinity of the distal end thereof, and means secured on the tubular shaft for preventing expansion of balloon segments wherein the tubular shaft comprises a guidewire lumen with an entry for the guidewire distal of the balloon and an exit for the guidewire distal of the proximal end of the tubular shaft and wherein the means for preventing expansion of balloon segments are attached to the tubular shaft either distal of the exit for the guidewire if said exit is proximal of the balloon or proximal of the exit for the guidewire if said exit is distal of the balloon;

the means for preventing expansion of balloon segments comprise a sleeve having proximal and distal ends one of which is surrounding a portion of the tubular shaft in the vicinity of the balloon and the other of which is surrounding a portion of the balloon; and latch means on one of the sleeve or shaft cooperating with catch means on the other of the sleeve or shaft for attaching one end of the sleeve to the portion of the tubular shaft surrounded by that end of the sleeve.

10. A balloon catheter comprising:

a tubular shaft having a proximal end and a distal end, an elongated dilatation balloon with proximal and distal ends, said balloon being mounted on said tubular shaft in the vicinity of the distal end thereof, and means secured on the tubular shaft for preventing expansion of balloon segments wherein the tubular shaft comprises a guidewire lumen with an entry for the guidewire distal of the balloon and an exit for the guidewire distal of the proximal end of the tubular shaft and wherein the means for preventing expansion of balloon segments are attached to the tubular shaft either distal of the exit for the guidewire if said exit is proximal of the balloon or proximal of the exit for the guidewire if said exit is distal of the balloon; and elastic balloon jacket means for enclosing a portion of the balloon, said jacket means having a proximal end and a distal end, and wherein one of said ends is disposed on the tubular shaft and the other of said ends is disposed on the means for preventing expansion of balloon segments.

11. A stent delivery system for a balloon expandable stent comprising:

a balloon catheter with a tubular shaft having a proximal end and a distal end, and an elongated dilatation balloon with proximal and distal ends, said balloon being mounted on said tubular shaft in the vicinity of the distal end thereof wherein the tubular shaft comprises a guidewire lumen with an entry for the guidewire distal of the balloon and an exit for the guidewire distal of the proximal end of the tubular shaft, and wherein means for preventing expansion of balloon segments are attached to the tubular shaft either distal of the exit for the guidewire if said exit is proximal of the balloon or proximal of the exit for the guidewire if said exit is distal of the balloon;

the means for preventing expansion of balloon segments comprise a sleeve having proximal and distal ends one of which is surrounding a portion of the tubular shaft in the vicinity of the balloon and the other of which is surrounding a portion of the balloon; and latch means on one of the sleeve or shaft cooperating with catch means on the other of the sleeve or shaft for attaching one end of the sleeve to the portion of the tubular shaft surrounded by that end of the sleeve.

12. A stent delivery system for a balloon expandable stent comprising:

a balloon catheter with a tubular shaft having a proximal end and a distal end, and an elongated dilatation balloon with proximal and distal ends, said balloon being mounted on said tubular shaft in the vicinity of the distal end thereof wherein the tubular shaft comprises a guidewire lumen with an entry for the guidewire distal of the balloon and an exit for the guidewire distal of the proximal end of the tubular shaft, and wherein means for preventing expansion of balloon segments are attached to the tubular shaft either distal of the exit for the guidewire if said exit is proximal of the balloon or proximal of the exit for the guidewire if said exit is distal of the balloon; and elastic balloon jacket means for enclosing a portion of the balloon, said jacket means having a proximal end and a distal end, and wherein one of said ends is disposed on the tubular shaft and the other of said ends is disposed on the means for preventing expansion of balloon segments.

* * * * *